US008435958B2

(12) United States Patent
Kunz et al.

(10) Patent No.: US 8,435,958 B2
(45) Date of Patent: *May 7, 2013

(54) METHOD FOR PRODUCING PECTIN HYDROLYSIS PRODUCTS

(75) Inventors: Markwart Kunz, Worms (DE); Mohammad Munir, Kindenheim (DE); Manfred Vogel, Neuleiningen (DE)

(73) Assignee: N.V. Nutricia, HM Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,222

(22) Filed: Apr. 25, 2011

(65) Prior Publication Data

US 2011/0195918 A1 Aug. 11, 2011

Related U.S. Application Data

(60) Division of application No. 12/416,803, filed on Apr. 1, 2009, now Pat. No. 7,960,351, which is a division of application No. 10/416,347, filed on Sep. 29, 2003, now Pat. No. 7,576,070, which is a continuation of application No. PCT/EP01/13508, filed on Nov. 21, 2001.

(30) Foreign Application Priority Data

Nov. 22, 2000 (DE) .................. 100 57 976

(51) Int. Cl.
*A61K 31/7012* (2006.01)
(52) U.S. Cl.
USPC .......................................... 514/23
(58) Field of Classification Search ............ 514/23
See application file for complete search history.

(56) References Cited

U.S. PATENT DOCUMENTS

| | | | |
|---|---|---|---|
| 2,164,186 A | 6/1939 | Brown et al. | |
| 2,697,049 A | 12/1954 | Brieghel-Muller et al. | |
| 2,774,693 A | 12/1956 | Brieghel-Mueller | |
| 3,834,941 A | 9/1974 | Schoenrock et al. | |
| 4,795,494 A | 1/1989 | Toth et al. | |
| 5,683,991 A | 11/1997 | Guggenbichler et al. | |
| 5,834,442 A | 11/1998 | Raz et al. | |
| 7,576,070 B2 * | 8/2009 | Kunz et al. | 514/54 |
| 7,960,351 B2 * | 6/2011 | Kunz et al. | 514/23 |
| 2008/0017187 A1 | 1/2008 | Deneus et al. | |
| 2009/0007902 A1 | 1/2009 | Ajdari Rad et al. | |

FOREIGN PATENT DOCUMENTS

| | | |
|---|---|---|
| DE | 4223613 | 1/1994 |
| DE | 103 50 672 A1 | 6/2005 |
| DE | 102006004103 A1 | 8/2007 |
| EP | 0 716 605 B1 | 6/1996 |
| JP | 4-36166 A | 2/1992 |
| JP | 4-141041 A | 5/1992 |
| JP | 5-115247 A | 5/1993 |
| JP | 5-238940 A | 9/1993 |
| JP | 6-217731 A | 8/1994 |
| JP | 9-208471 A | 8/1997 |
| JP | 9-208472 A | 8/1997 |
| JP | 9-208474 A | 8/1997 |
| WO | WO-01/60378 A2 | 8/2001 |
| WO | WO-2005/042787 | 5/2005 |

OTHER PUBLICATIONS

De Vries et al., Carbohydrate Polymers, 1982, 2, pp. 25-33.*
van Alebeek et al, The Journal of Biological Chemistry, 2002, 277(29), pp. 25929-25936.*
Lieker, et al., "Gewinnung von multifunktionellen Oligogalacturonsauren durch ensymatischen Abbau von Rubenpreb schnitzeln"; Zuckerind. 119 (1994) Nr. 5, S. 562-564.
Endreb, et al., Monitoring the Course of Enzymic Degradation of Pectic Substances by Automated Fast Ion Chromatography (FIC); Lebensm.-Wiss. u.-Technol., 24, No. 1, pp. 80-85 (1991).
Ohannesian, et al., "Galectins in Tumor Cells"; Glycosciences Status and Perspectives; pp. 459-466 (1997).
Helmut Uhlig; "Enzyme arbeiten fur uns—Technische Enzyme und ihre Anwendung"; pp. 121-122.
Biosis Prev 1999 00 13 51 04.
Chemical Abstracts 133:262932.
Chemical Abstracts 78:81371.
Biosis Prev 1999 00 32 37 96.
Biosis Prev 1995 98 07 68 30.
Derwent Abstract 1998-515105/44.
Derwent Abstract 1994-275514/34.
Gunther Winkelmann, "Microbial Degradation of Natural Products", VCH Verlagsgesellschaft mbH, Weinheim, Germany, pp. 58-67 (1992).
Visser et al, Eur. J. Biochem. 1999, 259, 577-585.
Voragen, Versi. Landbouk. Onderz, 1972, 780, 121.
Winkelmann, G., Microbial Degradation of Natural Products, VCH, Germany, 1992, 58-67.
Wilatts et al, Carbohydrate Research, 2000, 327, 209-320.
Endres et al Lebensmittel-Wissenschaft & Technologie, 1991, vol. 4(1), 80-85.
Kester et al The Journal of Biological Chemistry, 1999, 274(52), 37053-37059.
Van Der Poel et al., "Sugar Technology, Beet and Cane Sugar Manufacture", XP002496167, pp. 485, 488, 503-506 (1998).
Kraus et al., "Investigations of conditions for optimum colloid coagulation in preliming of beet juice", Zuckerind, vol. 122, No. 2, pp. 91-99 (1997).
Dr. Dietrich Becker, Dormagen, "Brieghel-Mueller predefecation", Zucker, No. 17, pp. 383-385 (Sep. 1952) (and English translation of same).
"Zur Frage der Vorscheidung (Concerning the question of predefecation)", Centralblatt fuer die Zuckerindustrie, No. 7, pp. 119-120 (1932) (and English translation of same).
English abstract of Mohsen Ajdari Rad, Inline-Online- erfass.
English translation of Japanese Office Action, dated Oct. 3, 2006.
The Merck Manual, 1992, pp. 24-25 and 77-86.

* cited by examiner

*Primary Examiner* — Shaojia Anna Jiang
*Assistant Examiner* — Ganapathy Krishnan
(74) *Attorney, Agent, or Firm* — Dickstein Shapiro LLP

(57) ABSTRACT

Methods for the production of pectin hydrolysis products, the pectin hydrolysis products produced in this manner, as well as their use are described.

18 Claims, No Drawings

METHOD FOR PRODUCING PECTIN HYDROLYSIS PRODUCTS

This is division of application Ser. No. 12/416,803, filed Apr. 1, 2009, now U.S. Pat. No. 7,576,070, which was a division of application Ser. No. 10/416,347, filed Sep. 29, 2003.

FIELD OF THE INVENTION

The invention relates to a method for producing pectin hydrolysates, in particular of a pharmaceutical or dietetic preparation for reducing and/or preventing the adhesion of pathogenic substances and organisms to eukaryotic cells, especially mammalian cells, or for inhibiting galectin-3-mediated cell-cell and/or cell-matrix interactions leading to the development of tumor diseases, methods for blocking the attachment of pathogenic substances or organisms to eukaryotic cells, methods for inhibiting galectin-3-mediated cell-cell and/or cell-matrix interactions, as well as pectin hydrolysates and preparations produced by using these methods.

BACKGROUND OF THE INVENTION

Pathogenic organisms, and also cell-damaging substances, first must adhere to the surface of the target cell in order to be able to cause infection or damage the attacked cell. This adhesion is mediated, for example, by a ligand-receptor relationship, whereby glycostructures play an important role. If these glycostructures are blocked at the target cell surface or at the ligand, an infection can be prevented.

Glycostructures also play an important role in the formation of tumors and metastases (Liotta et al., Annu. Rev. Cell Biol., 55 (1986), 1037-1057). The formation of tumors includes cellular interactions mediated by cell surface components, in particular carbohydrate-binding proteins. This mediates the adhesion of tumor cells by way of cellular adhesion molecules. Many stages in the formation of metastases also include cell-cell interactions or interactions between cells and the extracellular matrix (ECM) which are mediated by cell surface components. The extracellular matrix (ECM) consists mainly of laminin, fibronectin, and proteoglycanes, of which very many are glycosylated, and whose oligosaccharide side chains provide detection determinants for cellular adhesion molecules. Laminin is an N-bound glycoprotein with poly-N-acetyl lactosamine sequences. Metastatic spread occurs when circulating agglomerates of tumor cells, thrombocytes, and lymphocytes make contact in capillaries by way of adhesion molecules with the endothelium. This contact provides the signal for opening the endothelial cell functions. As a result, the tumor cells are able to bind to receptors on the basal membrane by way of additional adhesion molecules. After destroying the basal membrane, the tumor cells get direct access to the stroma, whereby again interactions occur between the laminin and fibronectin and the respective receptors, as was the case in the primary tumor invasion.

Important representatives of the carbohydrate-binding proteins are the galactoside-binding lectins galectin-1 and galectin-3 (Raz and Lotan, Cancer Metastasis Rev. 6 (1987), 433; Gabius, Biochim. Biophys. Acta, 1071 (1991), 1). It is known that galectin-3 promotes the embolic tumor dispersal in the circulation and increases the formation of metastases. Galectin-3 is expressed on the cell surface of many tumor cells, whereby the galectin-3 expression increases with progressing tumor development. Galectin-3 is also expressed by activated macrophages and oncogenically transformed cells or metastasis cells. Galectin-3 has a high affinity for oligosaccharides, which include polylactosamines, whereby galectin-3 binds in particular to two glycoproteins that occur in the form of several cell types, for example human colon cancer cells and human breast cancer cells. Another ligand for galectin-3 is, for example, laminin. Galectin-3, which is also expressed on the surface of endothelial cells, is also involved in the adhesion of tumor cells to endothelial cells.

U.S. Pat. No. 5,834,442 describes methods for treating cancers in mammals, in particular for treating prostate cancers, where the treatment of cancers, including the inhibition of the formation of metastases, is performed by oral administration of modified pectin, preferably water-soluble, pH-modified citrus pectin. To produce pH-modified pectin, a pectin solution is depolymerized by increasing its pH value to 10.0 and then reducing the pH value to 3.0. The modified pectin has a molecular weight of approximately 1 to 15 kd. Rats that were administered modified citrus pectin in their drinking water showed a significantly reduced formation of lung metastases compared to untreated control groups. In vitro experiments demonstrated that the adhesion of galectin-3-expressing MLL endothelial cells to rat aortic endothelial cells (RAEC) was almost completely inhibited in the presence of modified citrus pectin. Other experiments studied the effect of pH-modified citrus pectin on the colonization of MLL endothelial cells. The ability of cells to grow in semi-solid medium (anchorage independence) may be used as a criterion for cell transformation and the invasive potential of cells, since cell growth in a semi-solid medium requires cell migration and colonization. It was hereby found that modified citrus pectin was able to significantly reduce both the number of MLL colonies formed as well as their size. In the process, modified citrus pectin appears to have more of a cytostatics effect than a cytotoxic effect. The effect of modified citrus pectin on cell-cell interactions and cell-matrix interactions based on carbohydrate-mediated mechanisms, especially galectin-3-mediated interactions, were also investigated. It was found that, in contrast to non-modified citrus pectin, modified citrus pectin inhibited the adhesion of B16-F1 melanoma cells to laminin. Of laminin, it is known that it acts as a ligand for soluble galectin-3.

From EP 0 716 605 B1 it is known that the adherence of pathogenic agents, such as, for example, E. coli, to cells, in particular to epithelial cells of the gastrointestinal and genitourinary tract can be substantially (i.e., up to 90%) reduced with a specially prepared carrot soup, bladder tea, coconut milk, etc. According to this document, this effect can be attributed to the pectins contained in these plant products, which are essentially chains of 1,4-α-glycosidically bound galacturonides whose acid groups are esterified 20 to 80% with methanol and which, in addition to galacturonic acid, also may contain other sugar components, for example, glucose, galactose, xylose, and arabinose.

The document further describes that monogalacturonic acid shows no blocking of the adhesion, while a blocking of up top 91.7% or 84.6% can be found with digalacturonide and trigalacturonide respectively. This document clearly determines that the monomer galacturonic acid does not block the adhesion, and the desired blocking effect decreases along with an increasing molecular weight of the galacturonides. This means that the degree of polymerization of the desired galacturonides is DP 2 or 3. It is also required that the degree of esterification is <2%. The pectin hydrolysis products produced according to the method described in this document contain only very small portions of the di- and trigalacturonides designated as effective, however (approximately 12% related to the raw material). This production method wastes resources and causes environmental problems, because large quantities of unusable secondary products are created and must be disposed of.

The technical problem underlying the present invention therefore consists of providing additional methods and means for fighting infections and for reducing and/or preventing the adhesion of harmful, in particular pathogenic, substances and organisms to eukaryotic cells, in particular mammalian cells, as well for the blocking of interactions between mammalian cells, in particular tumor cells, which are mediated by carbohydrate-binding galectin-3 molecules located on the cell surface and are responsible for the development of, in particular, tumor diseases, in particular for the prevention of the formation of metastases in mammals.

This technical problem is solved with the methods according to the invention for the production of pectin hydrolysis products, which result in the production of oligogalacturonides with a monomer content as low as possible, a high content of molecules with at least one double bond each, as well as a degree of esterification of $\geq 20\%$, and which can be performed with a substantially higher yield than with the state of the art.

The problem is solved in particular in that an aqueous solution or suspension of a pectin or pectin-containing, in particular plant, material, preferably a pectin with a high degree of esterification, is treated in a first step with a first pectin-hydrolyzing enzyme A and then in a second step with a second pectin-hydrolyzing enzyme B. This yields a previously defined pectin hydrolysis product that has excellent properties as a means for reducing or preventing the adhesion for the life and/or proliferation functions of cells of harmful, for example pathogenic, allergenic, infectious, or toxic substances or organisms, for example microorganisms, such as yeasts, fungi, germs, bacteria, viruses, spores, viroids, prions.

Enzyme A may be, for example, a pectinlyase (EC 4.2.2.10) or endopolygalacturonase (EC 3.2.1.15), preferably a pectinlyase, however. Enzyme B may be an endopolygalacturonase or a pectinlyase, preferably an endopolygalacturonase, however.

SUMMARY OF THE INVENTION

According to the invention, it was unexpectedly found that galacturonides with double bonds in the molecule are especially effective in blocking the adhesion of, for example, pathogenic germs and cell-damaging substances to epithelial cells of the gastrointestinal and genitourinary tract. In addition, an especially efficient prevention and/or reduction, for example blocking, requires a higher degree of esterification, in particular $\geq 20$, preferably $\geq 30$, $\geq 40$, $\geq 50$, especially preferably $\geq 60$, $\geq 65$, $\geq 70$, or $\geq 71\%$. However, the method described in the state of the art only produces galacturonides that do not have any double bonds and are practically completely deesterified.

Within the context of the present invention, the term "degree of esterification" means that portion of acid groups of a galacturonide principally available for esterification that is esterified with an alcohol, especially methanol.

Within the context of the present invention, "unsaturated galacturonic acid molecules" are in particular 4,5-unsaturated galacturonic acid molecules.

DETAILED DESCRIPTION OF PREFERRED EMBODIMENTS

In one embodiment of the invention, the treatment with enzyme B is followed by a treatment with another, third enzyme C. This enzyme C may be a pectin esterase (EC 3.1.1.11). This makes it possible to adjust the degree of esterification of the products in an especially accurate manner.

Another embodiment of the invention provides that after completed enzymatic treatment according to the invention, the remaining, undissolved components are removed from the solution by centrifugation and/or ultrafiltration.

Another embodiment provides that the solution obtained after completed enzymatic treatment according to the invention and clarification by centrifugation or ultrafiltration is transformed by one of the actually known methods into its dry form, for example, into a ground, grainy, granulated, or powder form.

The solution obtained after the enzymatic treatment according to the invention, or the dry product obtained thereof, show a very good effect with respect to blocking the adhesion of, for example, pathogenic germs and cell-damaging substances to, for example, epithelial cells of the gastrointestinal and genitourinary tract in humans and animals. For this reason, they may be used in animal feed, for example by pig farmers to prevent diarrhea disorders in piglets.

The solution or suspension of the pectin or pectin-containing, preferably plant, material used according to the invention has a pH value in a range from 3.5 to 5.5 or/and in another preferred embodiment a pectin concentration of 3% to 25%.

The treatments with enzymes A, B, and possibly C take place at a pH value of 3.5 to 5.5 over a period of 2 hours to 24 hours at a temperature from 25° C. to 60° C. and a concentration of enzyme A, B, possibly C, of 10 to 30 ml/kg of pectin.

Another preferred embodiment provides that the content of galacturonides in the pectin hydrolysate (% by weight in relation to dry substance) is at least 60, $\geq 70$, $\geq 75$, $\geq 80$, or especially preferably at least 85% by weight.

Another preferred embodiment provides that in the pectin hydrolysate the content of carbohydrates with a DP-1 (monomers) in relation to the total carbohydrates of the pectin hydrolysate is <25, <20, <10, <8, <5, especially preferably <4% by weight (related to the dry substance).

Another preferred embodiment provides that the content of carbohydrates, in particular galacturonides with a degree of polymerization DP>10 in relation to the total carbohydrate content of the pectin hydrolysate, is less than 10, <8, especially preferably <5% by weight (related to the dry substance).

Another preferred embodiment provides that the content of unsaturated galacturonides in relation to the total content of galacturonides in the pectin hydrolysate is at least 10, preferably >15, >20, >25, >30, in particular 36.5% by weight to 46% by weight (related to dry substance).

In a preferred embodiment, the pectin hydrolysates produced according to the invention have a content of at least 60, $\geq 70$, $\geq 75$, $\geq 80$, or, especially preferably, at least 85% (related to dry substance) of carbohydrates, in particular galacturonides with a degree of polymerization of 2 to 10, preferably 3 to 8, especially preferably 4.5 (% by weight dry substance, related to the total carbohydrate content of the pectin hydrolysate).

In an especially preferred embodiment, the pectin used is citrus pectin, apple pectin, or sugar beet pectin.

In a preferred embodiment, the pectin-containing material used, in particular pectin-containing plant material, is apple pomace, sugar beet cossettes, or citrus pellets, i.e., dried residues, for example, from the production of orange juice, lemon juice and/or lime juice.

The pectin hydrolysates produced according to the invention, i.e., pectin hydrolysis products, are excellently suited as a pharmaceutical or dietetic preparation for fighting infectious diseases or/and for fighting the adhesion of harmful substances and/or organisms to mammalian cells, in particular human cells.

The pectin hydrolysates produced according to the invention are also excellently suited as a pharmaceutical preparation for inhibiting cell-cell interactions and/or interactions between cells and the extracellular matrix in humans or mammals, in particular such interactions mediated by galectin-3 molecules located on the cell surface. The pectin hydrolysis products according to the invention are therefore particularly suited for inhibiting cell-cell and/or cell/matrix interactions involving tumor cells, and which are therefore responsible for the development of diseases, especially tumor diseases, in humans or mammals. The pectin hydrolysates according to the invention therefore are also suitable as a pharmaceutical preparation for treating tumor diseases, especially for reducing the formation of metastases in cancers, since they prevent the galectin-3-mediated tumor cell adhesion and/or the invasive potential of the tumor cells.

The invention therefore also relates to the pectin hydrolysates obtained according to the invention, i.e., pharmaceutical preparations and dietetic preparations containing pectin hydrolysis products, which may be, for example, foods or snacks, such as dairy products, yogurt, cereals, baked goods, etc.

The invention also relates to the use of the previously mentioned pectin hydrolysis products for the production of pharmaceuticals that prevent the attachment or adhesion of harmful substances and/or organisms to mammalian cells, in particular human cells, in particular for fighting, i.e., prophylaxis and therapy, of infectious diseases, poisonings, allergies, etc.

The invention furthermore relates to the use of the previously mentioned pectin hydrolysis products for preventing the attachment or adhesion of harmful substances and/or organisms to mammalian cells, in particular human cells, in particular for fighting infectious diseases, poisonings, allergies, etc.

The infections fought according to the invention may be infections of the blood system, respiratory tract, genitourinary tract, nasopharyngeal space, or gastrointestinal tract.

Another field of use is human nutrition, where they are helpful, for example, in preventing diarrhea in infants, but also in adults.

The invention also relates to the use of the previously mentioned pectin hydrolysis products for inhibiting cell-cell interactions and/or interactions between cells and the extracellular matrix, in particular of such interactions mediated by carbohydrate-binding galectin-3 molecules located on the cell surface and which are responsible for the development of human and mammalian diseases, especially tumor diseases. These diseases include, in particular, prostate cancers, kidney cancers, Kaposi sarcomas, forms of chronic leukemia, breast cancers, breast adenocarcinomas, sarcomas, ovarian cancers, rectal cancers, throat cancers, melanomas, tumors of the small intestines, colon cancers, bladder tumors, mastocytomas, lung cancers, bronchial cancers, pharyngeal squamous cell carcinomas, gastrointestinal cancers, and stomach cancers. The pectin hydrolysis products according to the invention may be used in particular to reduce the invasive potential of metastasizing tumor cells and/or to inhibit the adhesion of tumor cells. It is preferred that the pectin hydrolysis products produced according to the invention are administered orally.

Another preferred embodiment of the invention relates to the use of the pectin hydrolysis products according to the invention for treating tumor diseases in humans or mammals.

The pectin hydrolysates according to the invention preferably may be used to treat tumors based on cell-cell interactions and/or interactions between cells and the extracellular matrix, in particular interactions mediated by carbohydrate-binding galectin-3 molecules located on the cell surface. By using the pectin hydrolysates according to the invention, preferably prostate cancers, kidney cancers, Kaposi sarcomas, forms of chronic leukemia, breast cancers, breast adenocarcinomas, sarcomas, ovarian cancers, rectal cancers, throat cancers, melanomas, tumors of the small intestines, colon cancers, bladder tumors, mastocytomas, lung cancers, bronchial cancers, pharyngeal squamous cell carcinomas, gastrointestinal cancers, and stomach cancers can be treated. The use of the pectin hydrolysates according to the invention for treating tumors specifically aims for the inhibition of adhesion of tumor cells and/or reduction of the invasive potential of metastasizing tumor cells.

The invention also relates to the use of the previously mentioned pectin hydrolysis products for producing a pharmaceutical preparation for inhibiting cell-cell interactions and/or interactions between cells and the extracellular matrix, in particular interactions that are mediated by carbohydrate-binding galectin-3 molecules located on the cell surface and that are responsible for the development of human or mammalian diseases, in particular of the previously described tumor diseases. The pharmaceutical preparation for inhibiting cell-cell interactions and/or interactions between cells and the extracellular matrix are preferably administered orally.

Another preferred embodiment of the invention therefore relates to the use of the pectin hydrolysis products according to the invention for producing a pharmaceutical preparation that may be used to treat the previously described tumor diseases, i.e., for tumors based on cell-cell interactions and/or interactions between cells and the extracellular matrix, especially interactions that are mediated by carbohydrate-binding galectin-3 molecules located on the cell surface. According to the invention it is provided that the pharmaceutical preparation may be used for reducing tumor growth and/or for reducing the formation of metastases, whereby the pharmaceutical preparation according to the invention prevents in particular the adhesion of tumor cells and/or reduces the invasive potential of tumor cells. The pharmaceutical preparation according to the invention is preferably administered orally.

The present invention also relates to a method for blocking the adhesion of harmful, in particular, pathological substances or organisms to cells of a human or mammalian body, comprising the administration of the pectin hydrolysis products produced according to the invention to a human or mammal in a quantity that is sufficient to block the adhesion of the harmful substances or organisms to mammalian cells and to prevent the development of an infection. The pectin hydrolysis products produced according to the invention are preferably administered orally.

The invention also relates to a method for inhibiting cell-cell interactions and/or interactions between cells and the extracellular matrix that are mediated by carbohydrate-binding galectin-3 molecules located on the cell surface and that are responsible for the development of human or mammalian diseases, in particular the previously mentioned tumor diseases, comprising the administration of the pectin hydrolysis products produced according to the invention to a human or mammal with a tumor disease in a quantity that is sufficient to reduce and/or to inhibit galectin-3-mediated cell-cell interactions and/or cell-matrix interactions. The pectin hydrolysis products produced according to the invention are preferably administered orally.

The present invention also relates to pharmaceutical preparations that contain the pectin hydrolysis products according to the invention in pharmaceutically or therapeutically effective quantities. In the context of the present invention, a "pharmaceutical preparation" is a mixture used for diagnostic, therapeutic, and/or prophylactic purposes that contains the pectin hydrolysis products according to the invention as active ingredients in a form that can be well administered in patients or mammals. The pharmaceutical preparation may be a solid or a liquid mixture. The expression "in pharmaceutically or therapeutically effective quantities" means that the active ingredients are contained in the pharmaceutical preparation in a dose that is sufficient to prevent the outbreak of a disease, for example, of an infectious disease or tumor disease, to heal the condition of such a disease, to stop the progression of such a disease, and/or to relieve the symptoms of such a disease. In addition to the pectin hydrolysis products according to the invention, the pharmaceutical preparations according to the invention in a preferred embodiment also contain pharmaceutically compatible vehicles, as well as diluents, release agents, lubricants, adjuvants, fillers, sweeteners, aromas, coloring agents, flavoring agents, or other pharmaceutically effective substances.

The dietetic preparations according to the invention also contain the pectin hydrolysis products in a pharmaceutically effective quantity.

Other preferred embodiments are described in the secondary claims.

The invention is explained in more detail in the following examples.

Example 1

0.3 ml of a pectinlyase (for example, Rohapect PTE by Röhm) were added to 1 l of citrus pectin solution (30 g highly esterified pectin in 1 l of water), and the solution was incubated with stirring at a pH 5.0 and 45° C. for 2 hours. Then 0.75 ml of an endopolygalacturonase (for example, Pectinase PL by Amano) were added and incubated under the same reaction conditions for another 3 hours. Then the enzymes were deactivated by heating to 95° C. The insoluble residue was removed by centrifugation, the clear solution was evaporated until dry, and the obtained solid was weighed. The weight was 25.8 g (corresponding to a yield of 75.6% related to used raw material).

The resulting product was analyzed using generally known analysis methods, and the following composition was determined:

| | |
|---|---|
| Carbohydrates DP1 | 3.6% |
| Galacturonides | 83.9% |
| of these: unsaturated (assumed mean DP = 4.5) | 46.0% |
| DP 2-10 | 80.4% |
| DP > 10 | 16.0% |
| Degree of esterification | 72.0% |
| Salt content | 3.0% |
| Raw protein | 1.7% |
| Water content | 4.6% |

Example 2

0.3 ml of a pectinlyase (for example, Rohapect PTE by Röhm) were added to 1 l of citrus pectin solution (30 g highly esterified pectin in 1 l of water), and the solution was incubated with stirring at a pH 5.0 and 45° C. for 2 hours. Then 0.75 ml of an endopolygalacturonase (for example, Pectinase PL by Amano) were added and incubated under the same reaction conditions for another 3 hours. Then the enzymes were deactivated by heating to 95° C.

The insoluble residue was removed by centrifugation and the clear solution underwent ultrafiltration (cut-off 10,000). The permeate was dried and yielded 22.8 g of solid matter (a yield of 66.8% related to used raw material).

| | |
|---|---|
| Carbohydrates DP1 | 3.0% |
| Galacturonides | 84.1% |
| of these: unsaturated (assumed mean DP = 4.5) | 36.5% |
| DP 2-10 | 93.0% |
| DP > 10 | 4.0% |
| Degree of esterification | 72.0% |
| Salt content | 6.7% |
| Raw protein | 1.3% |
| Water content | 4.4% |

Example 3

0.3 ml of a pectinlyase (for example, Rohapect PTE by Röhm) were added to 1 l of citrus pectin solution (30 g highly esterified pectin in 1 l of water), and the solution was incubated with stirring at a pH 5.0 and 45° C. for 2 hours. Then 0.75 ml of an endopolygalacturonase (for example, Pectinase PL by Amano) were added and incubated under the same reaction conditions for another 3 hours. Then 0.5 ml of a pectin esterase (for example, Rheozyme by Novo Nordisk) were added and incubated for another 45 minutes. Then the enzymes were deactivated by heating to 95° C. The insoluble residue was removed by centrifugation, the clear solution was evaporated until dry.

The resulting product was analyzed using generally known analysis methods. In contrast to Example 1, a degree of esterification of 35% was determined.

Example 4

Dried orange peel or citrus pellets were comminuted to a particle size of approximately 1-5 mm, and 100 g of this was stirred into 400 ml of water and left to soak. Then concentrated nitric acid (10 g) was added, and the suspension was heated to 85° C. and stirred at this temperature for 1.5 hours. This was followed by cooling to 45° C.; the pH value was increased with NaOH to 4.5, followed, after addition of 0.3 ml of a pectinlyase (for example, Rohapect PTE by Röhm), by 2 hours of incubation. Then 0.75 ml of an endopolygalacturonase (for example, Pectinase PL by Amano) were added and incubated under the same reaction conditions for another 3 hours. Then the enzymes were deactivated by heating to 95° C., concentrated, and the suspension was dried with a drum dryer.

Example 5

Dried orange peel or citrus pellets were comminuted to a particle size of approximately 1-5 mm, and 100 g of this was stirred into 400 ml of water and left to soak. Then concentrated HCl (8 g) was added, and the suspension was heated to 85° C. and stirred at this temperature for 1.5 hours. This was followed by cooling to 45° C.; the pH value was increased with NaOH to 4.5, followed, after addition of 0.3 ml of a pectinlyase (for example, Rohapect PTE by Röhm), by 2 hours of incubation. Then 0.75 ml of an endopolygalacturonase (for example, Pectinase PL by Amano) were added and incubated under the same reaction conditions for another 3 hours. Then the enzymes were deactivated by heating to 95° C., concentrated, and the suspension was dried with a drum dryer.

Example 6

Prevention of Adhesion of Pathogenic Germs in Human Epithelial Cells

For this test, human uroepithelian cells obtained by centrifugation from morning urine as well as two strains of *staphylococcus aureus* and *E. coli* were used, each as a suspension with $10^9$ germs/mL.

Test Procedure

Epithelial cells and germ suspension were incubated together at 37° C. for 30 minutes. The epithelial cells then were separated from the non-adherent germs by membrane filtration (8μ). The filters were washed several times, placed into normal saline, and the epithelial cells were suspended in it. After centrifugation of the suspension in saline, the pellet was applied to slides and stained according to May-Grünwald and Giemsa. The number of germs adhering to 50 epithelial cells were counted. This number represented the blank value. Epithelial cells to which no germ solution had been added were used as a control.

In the main test, epithelial first were incubated with aqueous solutions of various concentrations consisting of pectin hydrolysis products produced according to the invention (according to Example 1) for 1, 2 or 3 hours. They were then combined with the germ suspension and treated further as described above. The measuring value was obtained by counting the germs adhering to 50 epithelial cells.

Result

No reduction in the germ adhesion to the epithelial cells was observed for the "neutral" carbohydrates, such as raffinose, nystose, and isomelezitose used for comparison. By using the pectin hydrolysis products according to the invention, the adhesion of all tested microorganisms was almost completely prevented (blockage of >95%).

Example 7

1.5 g of the dried permeate from Example 2 were dissolved in 100 ml of 50 mM Nucleic acid-acetate solution with a pH value of 5.0 and were then given through a column (2.6×30 cm) that had been filled with the anion exchanger AG 1×2 (BioRad) and equilibrated with 50 mM Nucleic acid-acetate solution, pH value 5.0. The forerun from the column was analyzed with HPAEC (high performance anion exchange chromatography) and hydrolyzed for one hour with 1 N HCl at 95° C.

Result

In comparison with Raftiline (Orafti) as a standard, the oligosaccharides eluted from the column had a DP distribution of 2-12.

The analysis of the hydrolysates using a sugar analyzer (Biotronik) found primarily galactose (70%) as monosaccharides, as well as arabinose (23%), and traces of glucose and mannose. Overall, 8.3% of the galacturonide-containing products were obtained as neutral sugar-containing oligosaccharides in the forerun.

Example 8

Growth of Colon Cancer Cell Lines on Extracellular Matrix (ECM) in the Presence of Pectin Hydrolysate Human colon cancer cell lines HT-29 or Caco-2 were seeded with a cell density of $1 \times 10^4$ cells/ml in 15 mm Petri dishes and cultivated in medium RPMI 1640+10% fetal calf serum (FCS) (HT-29) or, respectively, in MEM+10% FCS (Caco-2) at 37° C. under an atmosphere containing 5% $CO_2$. The cells were left to grow for 1 to 2 days until reaching confluence. The dishes were then washed once with PBS, then incubated with PBS and 0.5% Triton X-100 for 30 minutes at room temperature on an agitator, and then washed 3 times with PBS. The previously described cell lines then were again seeded on the dishes with the ECM layers prepared in this way. The influence of the pectin hydrolysate on cell growth was determined by counting the cells. For this, the cells were again removed after 48 hours with trypsin/EDTA solution in HBBS (10 min) and were washed in PBS solution. Then the number of living cells was determined by staining with trypan blue solution (650 mg trypan blue in 400 ml 0.9% NaCl, 1:1 (v/v)) in a Neubauer counting chamber. As a control, experiments were performed with glucose. The results are shown in Table 1.

Table 1 shows that glucose had no influence on the growth of the HT 29 and Caco-2 cell lines, while pectin hydrolysate reduced cell growth in relation to the concentration used by up to 75%.

TABLE 1

| | Reduction in Cell Growth | | | |
| | HT 29 | | Caco-2 | |
| Concentration | Pectin hydrolysate | Glucose | Pectin hydrolysate | Glucose |
|---|---|---|---|---|
| 0.01% | 30% | 0% | 25% | 0% |
| 0.1% | 45% | 1% | 43% | 0% |
| 1.0% | 75% | 0% | 70% | 0% |

Example 9

Reduction of Invasive Capacity of Caco-2 Cells with Pectin Hydrolysate

The effect of pectin hydrolysate on the invasive capacity of Caco-2 cells was studied using the invasion test described by Erkell and Schirrmacher (Cancer Research, 48 (1988), 6933-6937). The test is based on the migration of cells through the pores of a nucleopore polycarbonate filter in a protein gel that contains several ECM proteins, such as, for example, type 1 and type III collagen, fibronectin, and laminin, to a nitrocellulose filter. The cells were added together with the pectin hydrolysate into a test system, after which the cells that had migrated through the protein layer were quantitatively evaluated in the lower nitrocellulose layer. As a control, the effect of glucose on the invasive capacity of Caco-2 cells was studied.

The results of these studies are shown in Table 2. The results show that the pectin hydrolysate according to the invention was able to reduce the invasive capacity of Caco-2 cells in part significantly in relationship to the concentration used, while glucose only caused a slight reduction of the invasive capacity of Caco-2 cells in higher concentrations.

|  | Reduction Of Invasive Capacity Of Caco-2 Cells | |
| --- | --- | --- |
| Concentration | Pectin Hydrolysate | Glucose |
| 0.01% | 30% | 0% |
| 0.1% | 69% | 2% |
| 1.0% | 88% | 3% |

Example 10

Anti-Galectin-3 Antibody Binding by Pectin Hydrolysate

The expression of galectin-3 on colon cancer cells was determined with immunofluorescence/flow cytometry methods using an anti-galectin-3-specific monoclonal antibody (mouse-Ig) and a corresponding anti-mouse FITC-coupled secondary antibody. Increasing concentrations of the pectin hydrolysate and of glucose as a control were incubated together with the primary antibody on the target cells, and then the inhibiting influence of the soluble sugar substance on the anti-galectin-3 binding was measured.

The influence of pectin hydrolysate on the anti-galectin-3 binding is shown in Table 3. Table 3 shows that glucose reduces the binding reaction of the monoclonal anti-galectin-3 antibody not at all or only slightly, while pectin hydrolysate reduces the binding of the antibody, in relation to the concentration used, in part substantially.

TABLE 3

|  | Reduction of Binding Monoclonal Anti-Galectin-3 Antibody | | | |
| --- | --- | --- | --- | --- |
|  | HT 29 | | Caco-2 | |
| Concentration | Pectin hydrolysate | Glucose | Pectin hydrolysate | Glucose |
| 0.01% | 34 | 0 | 28 | 0 |
| 0.1% | 67 | 0 | 63 | 0 |
| 1.0% | 85 | 2 | 82 | 0 |

The invention claimed is:

1. A composition comprising a dairy product containing a pectin hydrolysis product having a content of galacturonides that include at least one 4,5-unsaturated galacturonic acid molecule, wherein the galacturonic acid molecules are esterified >20% with methanol and wherein the pectin hydrolysis product has (1) a content of carbohydrates with a DP-1 of <25% by weight based on the total dry weight of carbohydrates or (2) a content of galacturonides of at least 60% by weight on the total dry weight of carbohydrates.

2. The composition according to claim 1, wherein the dairy product is a yogurt.

3. The composition according to claim 2, wherein the pectin hydrolysis product has a content of galacturonides of at least 60% by weight based on the total dry weight of carbohydrates.

4. The composition according to claim 2, wherein the pectin hydrolysis product has a content of galacturonides that include at least 10% in relation to the total dry weight of galacturonides of 4,5-unsaturated galacturonic acid molecules.

5. The composition according to claim 2, wherein the galacturonides are esterified $\geq$30% with methanol.

6. The composition according to claim 2, wherein the pectin hydrolysis product has a content of galacturonides with a degree of polymerization DP>10 in relation to the total carbohydrate content of the pectin hydrolysate is less than 10% by weight related on the dry substance.

7. The composition according to claim 2, wherein the pectin hydrolysis is produced by treating a pectin or pectin-containing plant material in aqueous solution or suspension with a pectinlyase and then with an endopolygalacturonase, and after said enzyme treatments, recovering the pectin hydrolysis product.

8. The composition according to claim 1, wherein the pectin hydrolysis product has a content of carbohydrates with a DP-1 of <25% by weight based on the total dry weight of carbohydrates.

9. The composition according to claim 4, wherein the pectin hydrolysis product has a content of galacturonides of at least 60% by weight based on the total dry weight of carbohydrates.

10. The composition according to claim 1, wherein the pectin hydrolysis product has a content of galacturonides of at least 60% by weight based on the total dry weight of carbohydrates.

11. The composition according to claim 1, wherein the pectin hydrolysis product has a content of galacturonides that include at least 10% in relation to the total dry weight of galacturonides of 4,5-unsaturated galacturonic acid molecules.

12. The composition according to claim 1, wherein the galacturonides are esterified $\geq$30% with methanol.

13. The composition according to claim 1, wherein the pectin hydrolysis product has a content of galacturonides with a degree of polymerization DP>10 in relation to the total carbohydrate content of the pectin hydrolysate is less than 10% by weight related on the dry substance.

14. The composition according to claim 1, wherein the pectin hydrolysis is produced by treating a pectin or pectin-containing plant material in aqueous solution or suspension with a pectinlyase and then with an endopolygalacturonase, and after said enzyme treatments, recovering the pectin hydrolysis product.

15. A method which comprises combining a pectin hydrolysis product having a content of galacturonides that include at least one 4,5-unsaturated galacturonic acid molecule, wherein the galacturonides are esterified $\geq$20% with methanol, with a dairy product.

16. The method according to claim 15 in which the pectin hydrolysis product has a content of galacturonides that include at least 10% in relation to the total dry weight of galacturonides of 4,5-unsaturated galacturonic acid molecules, and wherein the pectin hydrolysis product has (1) a content of carbohydrates with a DP-1 of <25% by weight based on the total dry weight of carbohydrates or (2) a content of galacturonides of at least 60% by weight based on the total dry weight of carbohydrates or both (1) and (2).

17. The method of claim 16 in which the dairy product is yogurt.

18. The method of claim 15 in which the dairy product is yogurt.

* * * * *